United States Patent [19]

Sawyer

[11] 4,167,045

[45] Sep. 11, 1979

[54] CARDIAC AND VASCULAR PROSTHESES

[75] Inventor: Philip N. Sawyer, Brooklyn, N.Y.

[73] Assignee: Interface Biomedical Laboratories Corp., Brooklyn, N.Y.

[21] Appl. No.: 827,952

[22] Filed: Aug. 26, 1977

[51] Int. Cl.² .......................... A61F 1/24; A61F 1/22
[52] U.S. Cl. ............................................. 3/1.4; 3/1;
 3/1.5; 3/1.7; 427/2; 427/250; 427/124;
 427/125; 427/430 R
[58] Field of Search ........................ 3/1.4, 1.5, 1, 1.7;
 427/2, 250

[56] References Cited

U.S. PATENT DOCUMENTS

| | | | |
|---|---|---|---|
| 3,276,448 | 10/1966 | Kronenthal | 3/1 X |
| 3,557,795 | 1/1971 | Hirsch | 427/2 X |
| 3,765,414 | 10/1973 | Arlen | 3/1 X |
| 3,840,391 | 10/1974 | Spitz et al. | 427/250 X |
| 3,918,099 | 11/1975 | Führ et al. | 3/1.4 X |
| 3,927,422 | 12/1975 | Sawyer | 3/1 |

OTHER PUBLICATIONS

Wesolowski et al., "Heterologous Aortic Grafts–With Special Reference to Recipient Site, Ethylene Oxide Freeze-Dry Preparation and Species of Origin," Ann. Surg. 145:187–198 (1957), [RD 1 A61].
Voorhees, Jr. et al., "The Use of Tubes Constructed From Vinyon "N" Cloth in Bridging Arterial Defects," Ann. Surg. 135:332–336 (1952), [RD 1 A61].
Sauvage et al., "Prosthetic Heart Valve Replacement," Ann. of N.Y. Academy of Sciences, 146:289–313 (1968).
Johnson et al., "Late Changes in Corona Vein Grafts," Am. Jour. of Cardiol. 26:640 (1970), [RC 681.A1 A56].
Edwards et al., "Aortic Valve Replacement with a Subcoronary Ball Valve," Sur. Forum 9:309–313 (1958), [RD 11 S8].
Sauvage et al., "The Healing and Fate of Arterial Grafts," Surg. 38:1090–1131 (1955), [RD 1 S78].
Szilagyi et al., "Long-Term Evaluation of Plastic Arterial Substitutes: An Experimental Study," Surg. 55:165–183 (1964), [RD 1 S78].
Ferguson, Jr., "Historical Use of Metals in the Human Body," Metals and Engineering in Bone and Joint Surgery, Williams and Wilkins Co., Balt. Chap. 1, pp. 1–18 (1959).
Hufnagel, "The Use of Rigid and Flexible Plastic Prostheses for Arterial Replacement," Surg. 37:165–174 (1955), [RD 1 S78].
Wesolowski et al., The Use of Artificial Materials in Surgery, "Current Problems in Surgery," Year Book Medical Publishers, Inc., Chicago (1966), pp. 1–86.
Vlodaver et al., "Pathological Changes in Aortic–Coronary Arterial Saphenous Vein Grafts," Circulation 44:719–728 (1971).
Starr, "Mitral Valve Replacement with Ball Valve Prostheses," British Heart Journal, 33 Supp. 47–55 (1971).
Sawyer et al., "New Approaches in the Selection of Materials Compatible with Blood," Artif. Heart Prog. Conf. Proc., Chap. 22, pp. 243–258 (1969).
Sawyer et al., "Long-Term Patency of Solid-Wall Vascular Prostheses," Arch. Surg. 91:735–742 (1965).
McCann et al., "Aluminum Prostheses as Blood Vessel Replacements," Surgery, vol. 61, No. 4, pp. 588–590, Apr. 1967.

*Primary Examiner*—Richard D. Lovering
*Attorney, Agent, or Firm*—Posnack, Roberts, Cohen & Spiecens

[57] ABSTRACT

A prosthesis suitable for implantation in a bloody environment. The prosthesis includes a surface material adapted for exhibiting a regular and periodic surface charge characteristic in the bloody environment. A prosthesis means supports the surface material and is adapted to perform a prosthetic function in the bloody environment. In cases where cross-linking is desired and the surface material cannot cross-link with the substrate material, an adaptive material is provided which cross-links both to the surface material and to the material of the prosthesis. In one type of prosthesis, the surface material is aluminized. In another type of prosthesis, acrylamide is applied to the prosthesis. In still another type of prosthesis, agar is applied to the prosthesis in conjunction with gelatin. In another type of prosthesis, albumin is applied to the prosthesis.

2 Claims, 10 Drawing Figures

CARDIAC AND VASCULAR PROSTHESES

FIELD OF INVENTION

This invention relates to cardiac and vascular prostheses and methods of making the same and materials therefor.

BACKGROUND OF THE INVENTION

The major emphasis in early research on implants was performed within the field of orthopedics. (Bechtol, C. D., Ferguson, Jr., A. B., and Laing, P. G. *Metals and Engineering in Bone and Joint Surgery.* Williams and Wilkins Co., Balt. Chapter 1, 1-18 (1959); Scales, J. T. *Arthroplasty of the Hip Using Foreign Materials:* A History, Paper 13, A Symposium, Institute of Mechanical Engineers, Vol. 181 Part 3J, 63-84, (1967); Weisman, S. *Metals for Implantation in the Human Body.* Ann. N.Y. Acad. Sci. 146, 80-95, (1968)). The most significant addition to implant surgery in the last twenty years has been the development of prostheses for vascular and cardiac reconstruction (Wesolowski, S. A., Martinez, A., and McMahone, J. D. *The Use of Artificial Materials in Surgery,* "Current Problems in Surgery." Year Book Medical Publishers, Inc., Chicago (1966). A major problem involved in the use of prosthetic alloplastic materials has been severe occlusive thrombogenicity (Hufnagel, C. A. *The Use of Rigid and Flexible Plastic Prostheses for Arterial Replacement, Surgery,* 37:165, (1955)). The search for acceptable materials and designs for vascular prostheses was of great importance because of a number of problems which were encountered with the use of polymeric and metal prostheses, autologous, homologous and heterologous bypass grafts in man. (Johnson, W. D. Auer, J. E. and Tector, A. T., *Late Changes in Coronary Vein Grafts Am. Jour. of Cardiol.* 26:640, (1970). and *Artegraft Conference,* Johnson and Johnson, Toronto, Ontario, Canada. June 23, (1973)).

Following the development of open heart surgery, an enormous effort was made in the field of prosthetic heart valves. The first successful development in this area was made by Goodman, Berg and Stuckey (Wesolowski, S. A. et al *The Use of Artificial Materials in Surgery,* "Current Problems in Surgery" Year Book Medical Publishers, Inc., Chicago (1966)). They produced the first completely thromboresistant prosthetic heart valve. This valve was later improved by Dr. Albert Star and Edwards Laboratories (Edwards, W. S. and Smith, L. *Aortial Valve Replacement with a Sub Coronary Ball Valve. Sur. Forum* 9:309 (1958); Starr, A. *Mitral Valve Replacement with a Ball Valve Prosthesis. British Heart Journal,* 33 Supp. 47 (1971). A number of valves were further developed by several corporations. These included the Bjork-Shiley valve which is the most successful of the prosthetic heart valves available today. More recently, glutaraldehyde tanned porcine collagen prosthetic heart valves developed by the Hancock Laboratory (Sauvage, L. R., Wesolowski, A. S., Sawyer, P. N. et al. *Prosthetic Valve Replacement Ann. of the N.Y. Academy of Sci.* 146:289 (1968)) have proven useful. They are resistant to intravascular thrombosis and have maintained their tensile strength following several years of implantation in man. Thus, a host of glutaraldehyde tanned collagen valvular prostheses have proven useful in man with respect to long term function and resistance to thrombosis.

Early attempts to replace blood vessels in man involved the use of rigid tubes of gold, silver, aluminum, magnesium, as well as the later development of polyethylene and polymethyl acrylic tubes (Szilagyi, D. E. *Long Term Evaluation of Plastic Arterial Substitutes: An Experimental Study, Surg.* 55:165 (1964); Woodward, S. C. *Biological End Points for Compatibility, Plastics in Surgical Implants* ASTM-STP 386, *A Symposium on Surg. Implants,* Indianapolis, Indiana (1964); Sawyer, P. N. Wu, K. T., Wesolowski, A. S., Brattain, W. H. and Boddy, P. J. *Long Term Patency of Solid Wall Vascular Prostheses, Arch. Surg.* 91:735, (1965)). In the majority of cases, these prostheses did not function satisfactorily. A major breakthrough came in 1952 when Voorhees and Blakemore described their experiments with a cloth prosthesis of Vinyon. (Voorhees, A. B., Jr., Jaretski, 111, A. and Blakemore, A. H. *Use of tubes constructed from Vinyon-*"N" *Cloth in bridging Arterial Defects.* Ann. Surg. 135;332 (1952)). This material was easy to handle, preclottable and resistant to thrombosis following implantation, although tensile strength, in situ, was lost with the passage of time. Preclotting the graft with the patient's blood produced a compound prosthesis, whereby, the lumen was covered by a fibrous neointima and the adventitia was enclosed by a fibrous capsule, which resulted in a well tolerated graft. Presently, the Decron graft is considered to be the most successful cloth type graft. (Sawyer, P. N. et al. *Vascular Graft Symposium, Current Status and Future Trends. NIH* (1976)).

Early attempts at vessel substitution with materials of biologic origin were carried out using arteries from cadavers (Wesolowski, S. A. and Sauvage, L. R. *Heterologus Aortic Hetergrafts with Special Reference to Recipient Site, Ethylene Oxide Freeze Dry Preparation and Specied of Origin, Ann. Surg.* 145:187 (1957). On the whole, these homografts functioned well for a period of time, but were soon replaced by fibrous tissue and calcium salts. This resulted in an inelastic structure, susceptible to thrombus, fracture, and aneurysm formation (Sauvage, L. R. and Wesolowski, A. S. *Healing and Fate of Arterial Grafts, Surg.* 38:1090 (1955)).

Following failure of the homografts, autografts from a patient's veins (saphenous) were used. Currently, the implantation statistics show that the saphenous vein is superior to synthetic implants (Sawyer, P. N. et al, *Vascular Graft Symposium,* Sauvage, L. R. and Wesolawski, A. S. *Healing and Fate of Arterial Grafts,* supra, and Vlodaver, C. and Edwards, J. E. *Pathological Changes in Aortocoronary Arterial Saphenous Vein Grafts. Circulation* 44:719 (1971)). When the saphenous vein is not available, i.e., the question arises as to which implant should be used. Experience has shown that a vascular graft must: (i) have an appropriate porosity (10,000-20,000 ml of water/square cm/minute) (Sawyer, P. N., Wu, K. T., Wesolowski, S. A. Brattain, W. H. and Boddy, P. J. *An Aid in the Selection of Vascular Prosthesis. Proc. Natl. Acad. Sci., U.S.A.,* 53:1965.), (ii) be blood compatible, (iii) possess tensile strength and (iv) be easy to handle with respect to sewing characteristics (Sawyer, P. N. and Srinivasan, S. *New Approaches in the Selections of Materials Compatible with Blood. Artificial Heart Prog Conf Proc Chapter* 22, 1969).

In a effort to overcome the problems of porosity, junctional thrombosis, and small diameter compliance exhibited by most implants in the periphery, I have conducted research on copolymeric collagen remnants from bovine carotid and brachial arteries. The collagen remains intact following enzymatic digestion (ficin) and is then glutaraldehyde tanned and negatively charged.

When implanted, these grafts reveal a striking tendency to remain thromboresistant and maintain their tensile strength as opposed to other commercially available collagen grafts that possess a limited degree of patency with early loss of tensile strength. My copolymeric grafts have remained patent in the femoral-popliteal, carotid and coronary positions (*Vascular Graft Symposium, supra*).

As to way these types of grafts perform so well, conclusive answers are not yet available. Scanning electron microscopic studies indicate that when the grafts fail, they become occluded by an atypical thrombus. It is therefore obvious that the success of this type of graft depends upon (i) the surface modification characteristics of the collagen (ii) blood interfacial reactions' occurring, (iii) structural aspects of the collagen surface.

SUMMARY OF THE INVENTION

I have heretofore developed a negatively charged, glutaraldehyde-tanned collagen copolymeric vascular bypass graft. This new graft appears to be superior to other commercially available bypass heterografts based upon life analysis tables. The processes used to chemically modify the collagen are uniquely versatile.

I am now working with second and third generation grafts and have produced Dacron hybrid grafts of several types. The application of this graft is aimed at specific clinical problems where the saphenous vein or conventional heterografts would be considered unsatisfactory. The hybrid graft can also be applied to the total artificial heart and bypass pump chambers and Dacron skirt of heart valves providing a more satisfactory blood compatible surface.

Dacron vascular grafts have been altered, in accordance with the invention, by coating them and filling their interstitial spaces with a variety of agents, in a variety of ways, to produce grafts with superior anti-thrombogenic characteristics.

The techniques utilized include: (1) copolymerization of proteins to the Dacron with glutaraldehyde and subsequent negative charging, (2) aluminization of the grafts, (3) the deposit of substances which may accept from a bloody environment materials which are compatible with the environment.

It is an object of the invention to provide an improved prosthesis material for making an improved prosthesis and method for making the same.

It is another object of the invention to provide for improved prosthesis characteristics in a blood environment.

To achieve the above and other objects of the invention, there is provided a prosthesis suitable for implantation in a bloody environment, said prosthesis comprising a surface material adapted for exhibiting a regular and periodic surface charge characteristic in said bloody environment, and prostheses means supporting said surface material and adapted to perform a prosthetic function in this environment.

In accordance with one embodiment of the invention, the surface material may be aluminum. In accordance with another embodiment, the surface material may be albumin. In accordance with still other embodiments, the surface material may be agar or acrylamide.

In accordance with one aspect of the invention, the prosthetic means is of a material normally incapable of cross-linking to said surface material. In this case, there is provided an adaptive material to cross-link to the material of said prosthetic means and to said surface material to provide architectural continuity therebetween while preserving said surface charge characteristics.

In accordance with the invention and the preferred embodiment thereof, the surface charge is preferably equivalent to approximately one electron per thousand square Angstroms in a regular three-dimensional pattern.

According to the invention, there is provided a method for preparing a prosthesis for functioning in a bloody environment with minimal thrombogenicity. This method comprises depositing on the surface of the prostheses a material adapted for exhibiting a regular and periodic thrombosis resistant surface charge in the bloody environment. Thus, for example, a synthetic material may be adapted for use as a prosthetic material which is adapted to function in a bloody environment. This may be achieved, for example, by metallizing the material at the surface thereof.

According to one embodiment of the invention, the metallizing may take place by the vapor depositing of aluminum on the surface.

According to another embodiment, the aluminum may be sprayed in an aerosol on the surface.

The prosthesis may be, for example, of woven Dacron. Thereupon may be deposited a surface material in the form of albumin, combined with gelatin. The thusly coated prosthesis may, for example, thereafter be treated with glutaraldehyde. The material deposited on the prosthesis may be, for example, of the general category of proteins and may be applied preferably in, for example, about a 3% solution.

According to the further feature of the invention, a thusly coated prosthesis may be further treated with a succinic compound.

According to still further aspects of the invention, the material may be applied by immersing the prosthesis in a slurry of agar. As an alternative, the prosthesis may be immersed in a solution of acrylamide.

The above and further objects and features of the invention will be found in the detailed description thereof as follows hereinafter.

BRIEF DESCRIPTION OF DRAWING

Figure 1A:
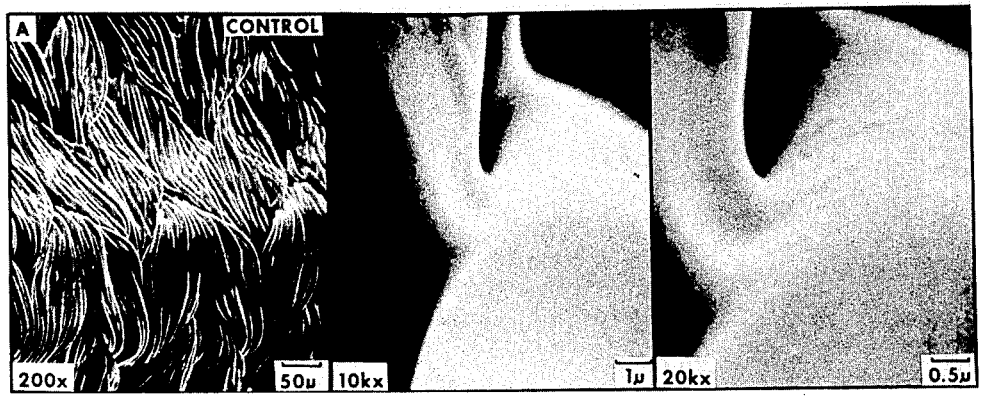
Figure 1B:
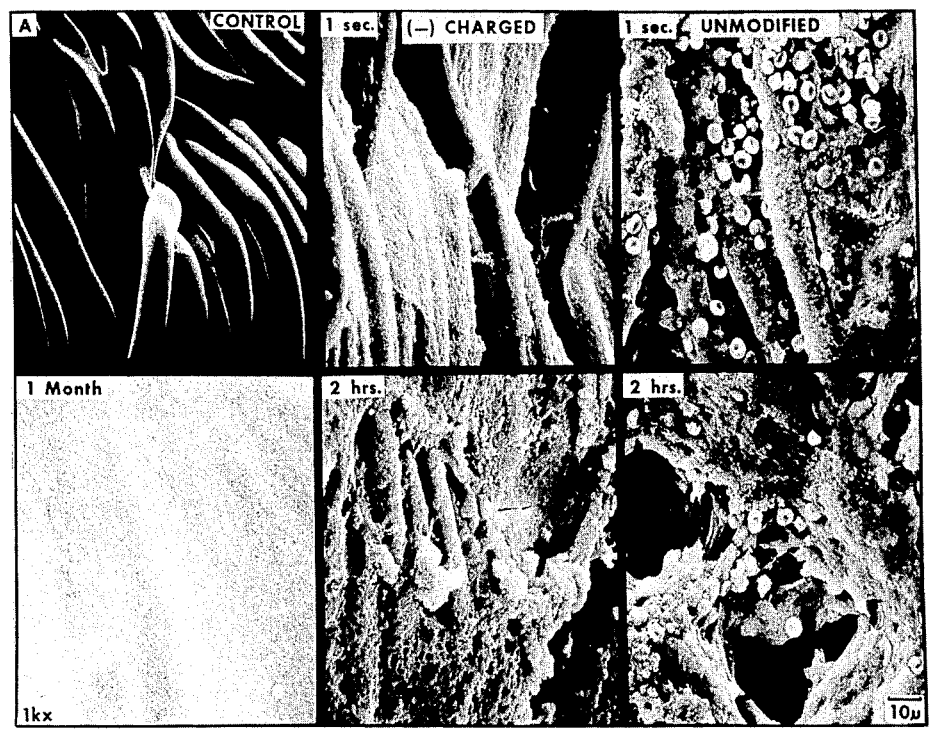
Figure 2A:
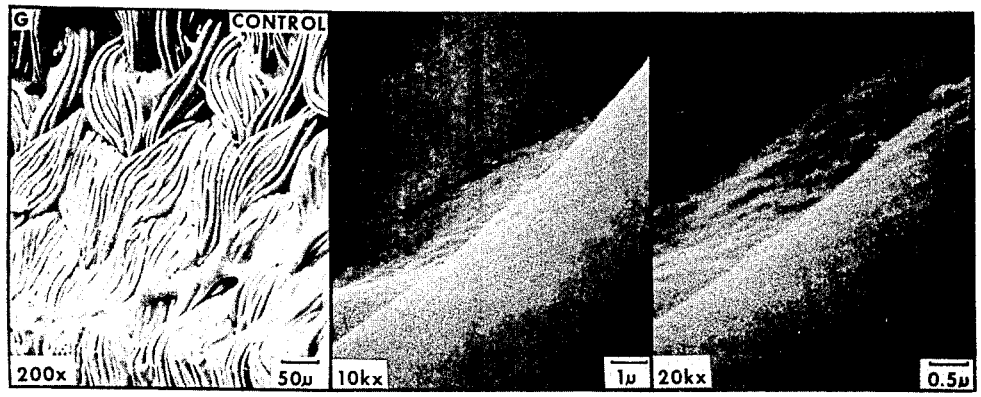
Figure 2B:
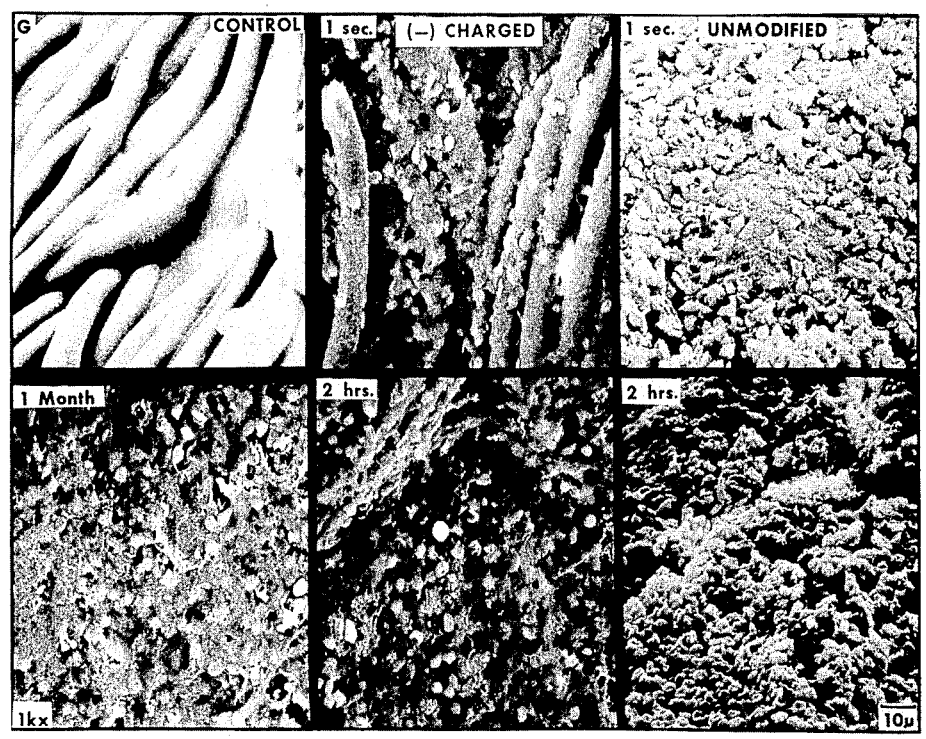
Figure 3A:
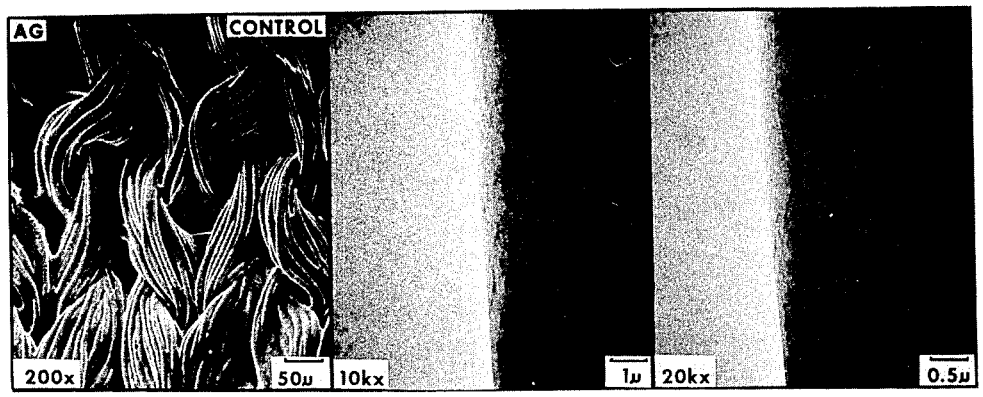
Figure 3B:
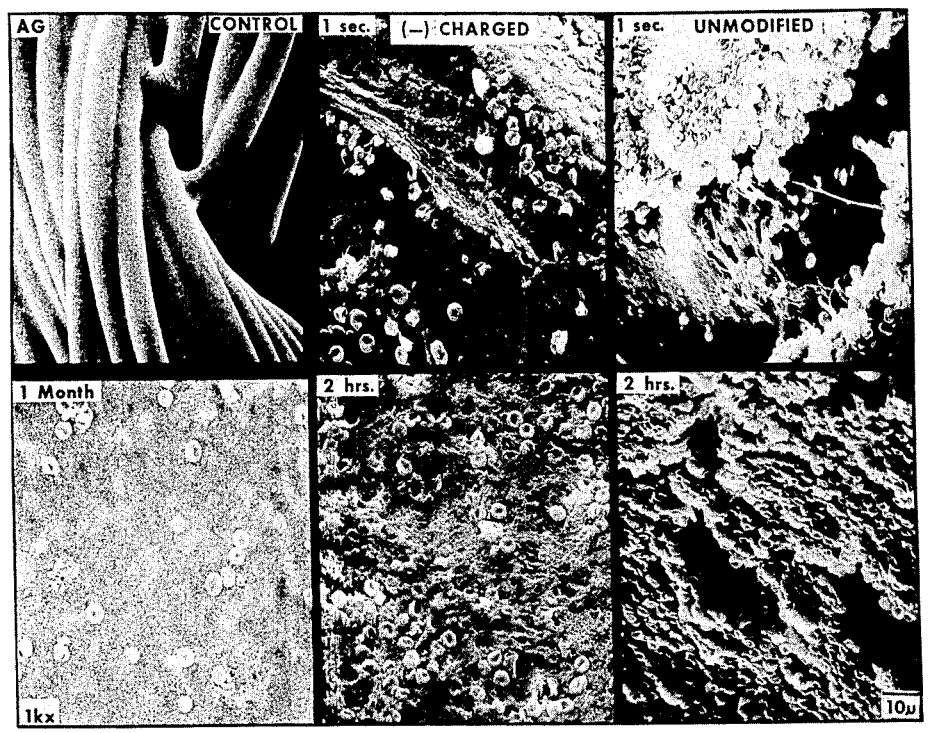
Figure 4:
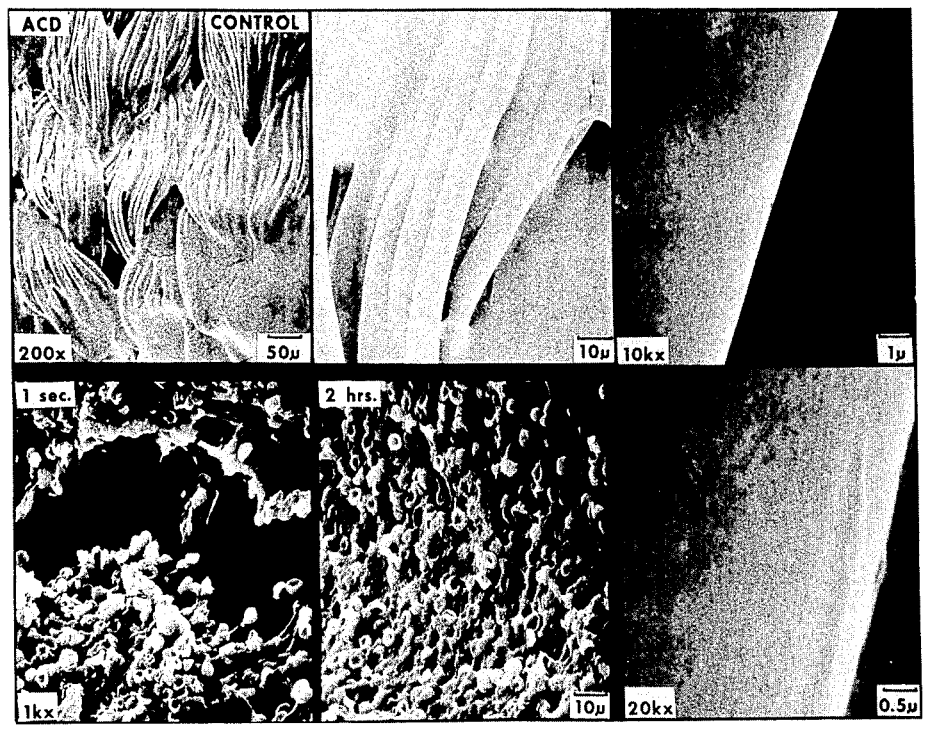
Figure 5:
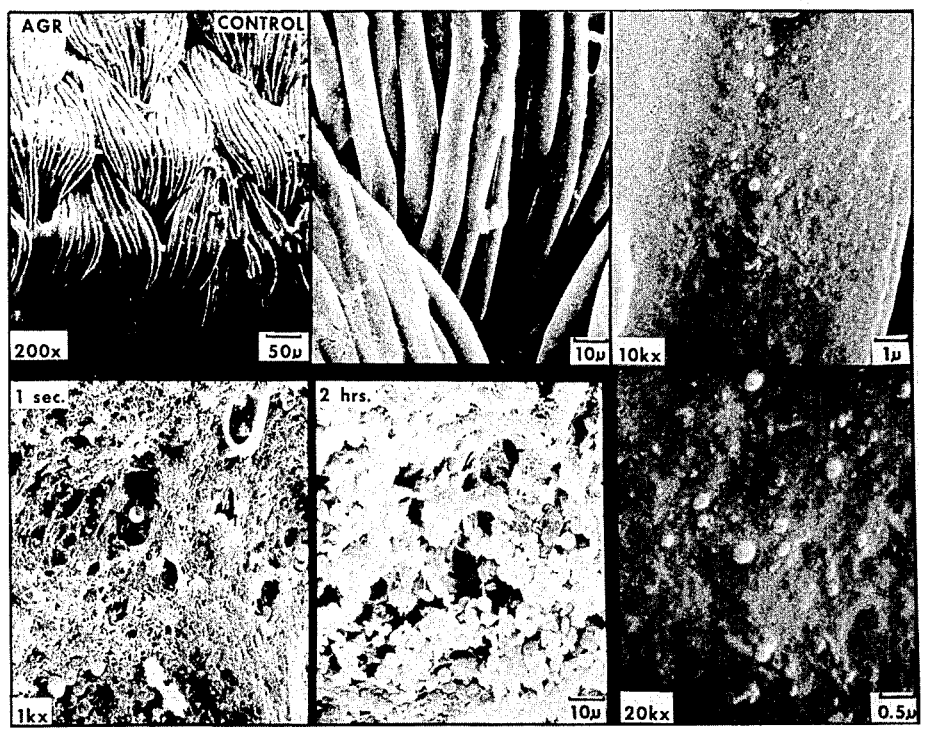
Figure 6A:
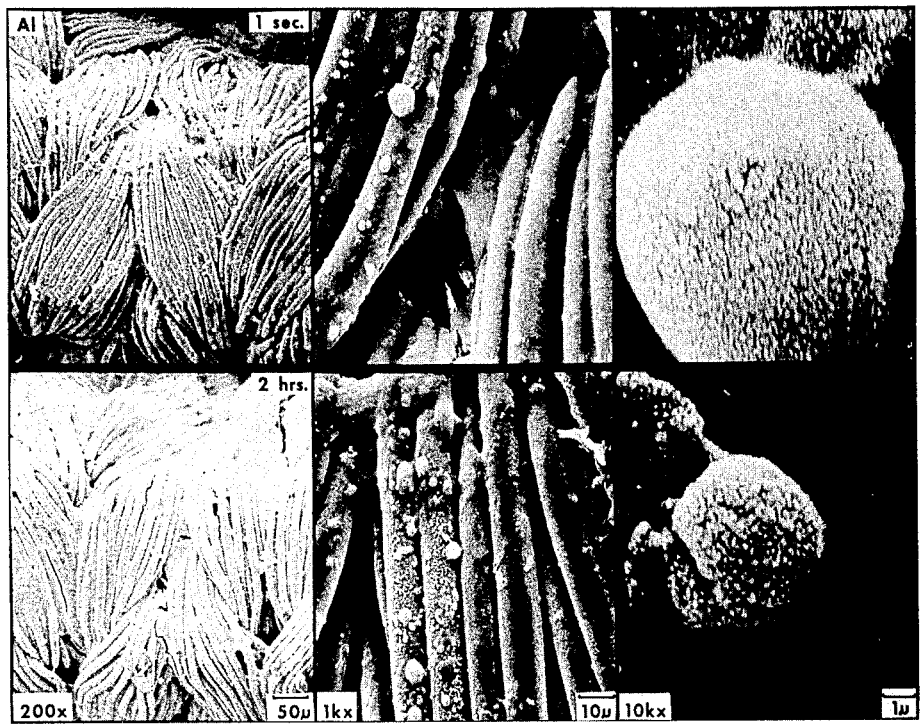
Figure 6B:
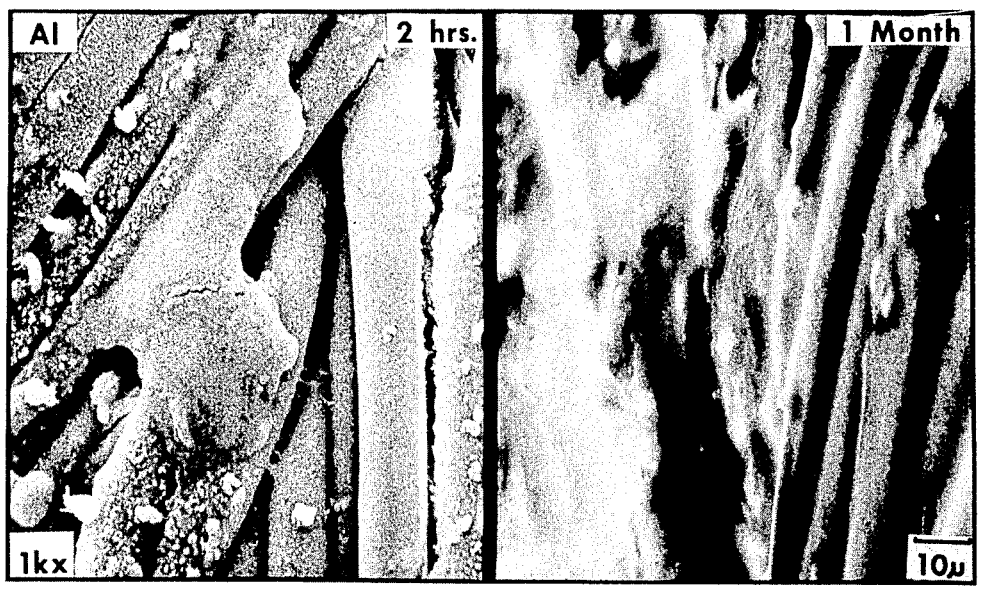

IN THE DRAWING:

FIG. 1(A) is a scanning electron microphotograph group of a polarized protein;

FIG. 1(B) is a collection of scanning electron micrographs of a protein-gelatin Dacron hybrid graph;

FIG. 2(A) shows scanning electron micrographs of a gelatin-Dacron hybrid graft;

FIG. 2(B) is a group of scanning electron micrographs of a gelatin-Dacron hybrid graft;

FIG. 3(A) shows the structure of an agar coated graft;

FIG. 3(B) shows the implantation results of a protein-gelatin Dacron hybrid graft;

FIG. 4 is a group of scanning electron micrographs of an aluminum coated Dacron hybrid graft;

FIG. 5 shows scanning electron micrgrphs of an agar coated Dacron hybrid graft;

FIG. 6(A) shows an aluminum coated Dacron prosthesis exposed to blood for one second; and FIG. 6(B) shows further magnification of the prosthesis illustrated in FIG. 6(A).

DETAILED DESCRIPTION

As has been stated hereinabove, the invention relates to the provision of a prosthesis having the capability of functioning in a bloody environment. The prosthesis may be of varying types but it can be, for example, a vascular prosthesis consisting of a tube adapted to function as a connection for bypass or a valve functioning to operate in the cardiac environment.

The invention is based in general on having the prosthesis exhibit a regular and periodic negative surface charge characteristic in the preferred case approximating one electron per thousand square Angstroms of surface in a regular three-dimensional pattern. Under certain circumstances, the regular and periodic surface charge may be positive.

A surface material will generally be employed to exhibit the above-noted characteristic. For this reason, the present invention is concerned with hybrid prostheses which are prostheses consisting of a basic material forming a prosthesis so that it is capable of performing the desired function and a surface material which exhibits the aforenoted charge.

In case the basic material is incapable of cross-linking with the surface material, an adaptive material may be provided to offer architectural continuity and cross-link the surface material and the supporting material by being adapted to cross-link itself respectively to each of these materials.

The invention offers, for example, copolymerization for a form of protein deposition, metallizing, agar application in the form of a uniform coating and the application of, for example, acrylamide. The invention offers further selective processing of certain of the above materials by treatment with succinic acid or the like or, for example, by treatment with glutaraldehyde.

The following are details of materials and methods which may be employed in accordance with the above:

Copolymerization (a method of protein deposition)

Fraction V Albumin (purified bovine or other mammalian albumin) purchased from Sigma Corporation, St. Louis, Mo., was dissolved (1, 3, 5 and 10 grams in 100 ml. of water) to produce several solutions of 1%–10% with distilled and deionized water. Gelatin (cutaneous), purchased from Baker Corporation,* was dissolved at room temperature in water, producing solutions ranging in concentration (1, 3, 5 and 10 grams in 100 mil. of water) from 1%–10%.
* J. T. Baker Chemical Co., Phillipsburgh, N.J.

A Microknit ® knitted or woven vascular prosthesis (Golaski Labs. Inc. of Philadelphia, Penna.) possessing 18 ridges to the inch (50 interstices per inch) was cut into 10 cm. segments (collapsed length) and cleaned in distilled and deionized water. It is then immersed in 10–20% (preferably 20%) glutaraldehyde (purchased from Electron Microscope Science Corporation of Fort Washington, Penna.) with distilled and deionized water (40 mls. of 50% glutaraldehyde in 60 mls. of water) and was allowed to stand for three hours.

The graft materials were then immersed in the appropriate protein (albumin, gelatin, collagen or the like) solution until thin (1 to 2,000 microns) coats of polymerized protein surrounded the Dacron tube. They were then suspended in air at room temperature and rinsed with water at room temperature for a minimum of 2 minutes. Care was taken to rinse the lumen of the grafts with water. The graft-protein "hybrid" prostheses were then reintroduced into fresh (20%) glutaraldehyde (40 mls. of 50% glutaraldehyde in 60 mls. of water) for 5–15 minutes. The process was repeated several times (three to ten times) until thin (1 to 2000 microns), uniformly coated grafts with their interstitial spaces filled were produced.

Dacron Backbone Structure

Several types of grafts and varying concentrations of proteins were utilized to determine optimal reaction conditions. They included 3 and 6 mm. I.D. (2–20 mm. is the range), 18 and 32 ridges/inch (10–32 ridges would be the range), and 1, 3, 5 and 10% protein solutions. It was found that the grafts possessing 18 ridges/inch (half crimp) were the optimal type of graft to modify, as they possessed the best surface configuration to provide for an even deposition of protein. The grafts having 32 ridges/inch (full crimp) had to be stretched on a glass rod of the same I.D. as the grafts in order to coat them properly. This prevented intra lumen coating and produced cracking when the rod was removed and the grafts regained their original shape. It was further that a 3% solution of protein provided the most effective coating both in optimizing time to coat and in thickness. One percent took a much longer time period to coat (greater than 1 hour). A 10% coating was achieved within 30 seconds but was very thick and did not permit obtaining the amount of flexibility required. In the aforegoing, the range of depth of the crimps is about 1 to 2 mm. and the wall thickness of the grafts is about ½ to 1 mm.

Using the techniques described above (i.e., 3% protein solutions and half crimped grafts) it was possible to coat both 3 mm. and 6 mm. I.D. grafts without difficulty.

Chemical Modification

The protein copolymerized hybrid grafts were further modified to enhance their net negative surface charge.

The end terminal amino acid residues were covalently coupled to succinic acid under acetylation reaction conditions (see U.S. Pat. No. 3,927,422). The grafts were rinsed thoroughly with distilled deionized water, and placed into a 10% (8–10% range) sodium bicarbonate buffer at a pH 8.5 (8.2–8.7 range) (8–10 grains in 100 mls. of water). The grafts were allowed to equilibrate with the buffer (5–30 minutes at 17°–27° C.) then ground solid succinic anhydride was added in 5 gm. portions (range 2–5 grams) to the buffer such that the final succinate solution concentration would be 1 M, (range: 1 to 5 molar) (2 to 8 micromoles of succinate per gram of protein).

The reaction was sufficiently vigorous to perfuse the lumen of the grafts. Several aliquots (range: 3 to 5) of the solid anhydride were added directly into the lumens of the grafts which were then placed into the buffer.

At the conclusion of the reaction (i.e., cessation of effervescence), the grafts were retested on a Zarb hydrostatic testing apparatus to ascertain structural integrity of copolymerization. The grafts were recoated if necessary and then stored and sterilized in 10% (range 3–10%) glutaraldehyde.

Acrylamide Hybridization

Acrylamide was prepared in accordance with the methods of Davis et al. A solution which would yield 7% (range: 5 to 8%) gel was utilized. The graft was immersed into solution and was allowed to polymerize. The graft was removed, washed with distilled deionized water and stored in 40% ETOH and water.

More particularly, a 20 ml. solution of 28.0 gms. of acrylamide (Bio-Rad Labs of Richmond, Ca.) and 0.735 grms. of bis-acrylamide (Bio-Rad Labs of Richmond, Ca.) were added to a 20 ml. solution containing 1 N. HCl, 48.0 ml./100 ml., 36.3 gms/100 ml. of TRIS (Bio-Rad Labs of Richmond, Ca.) and 0.723 mls. of TEMED/100 ml.

A segment of graft material was added to the acrylamide solution and allowed to equilibrate for one hour (½–1 hrs. at room temperature). At that time, a 40 ml. solution of ammonium persulfate, 1 mg/ml., (Bio-Rad Labs of Richmond, Ca.) was added to the acrylamide-bis-acrylamide solution in order to polymerize the solution. The solution was allowed to gel at room temp. for ½ hour (range: 10–40 min.). During this time interval, the graft was removed and reintroduced into the gelling medium 10 (range: 10 to 20) times. The graft was removed after the solution began to gel but before a solidified gel could form. The graft was then placed into a new test tube, and the acrylamide which had coated the Dacron fibers was allowed to gel. After the acrylamide polymerized, the graft was perfused with water at room temperature for 1 hour (range: ½ to 1 hour).

Agar Hybridization

A 3% agar-water mixture (Difco Labs, Detroit, Mich.) was made and heated to 100° C. until a uniform (aggregate free) slurry was evident. The graft material, washed three to ten times in distilled and deionized water, was immersed in the agar slurry until it was uniformly coated (100°–2,000 microns). It was then kept at 4° C. (range: 4°–10° C.) until the agar congealed. The graft was removed, washed and stored in 40% ethanol-H₂O until used.

Method of In Vitro Testing

All hybrid grafts underwent hydrostatic testing using a Zarb hydraulic pressure tester. The criterion used was the ability to withstand 30 mm (range 20–50) of Hg pressure without showing evidence of air leaks through the graft pores.

If a graft failed because of leaks during the test procedure, it was recoated by the process described above until there was no evidence of leakage. The hybrid grafts were stored in 10% glutaraldehyde until used.

Aluminization

Two techniques of coating a Dacron prosthesis with aluminum were utilized. They were: (1) vapor deposition and (2) hot plasma spray technique.

Vapor Deposition

Vapor deposition was accomplished in vacuum at $10^{-5}$ Torr. The aluminum vapor was forced through a small opening (0.25 to 20 mm.) in a heat shield and deposited on a Dacron graft in a thin, uniform coat of ½ to 10 microns. This technique proved to be the best technique for coating Dacron tubular material with aluminum as it provides a vapor which coats the graft completely without localized over concentration.

Hot Plasma Spray

Aluminum powder is heated to its melting point and is then sprayed by a pressurized aerosol-like container. This is repeated until a thin coating (½ to 10 microns) of aluminum is observed on the Dacron.

Implantation Studies

Implantation studies were divided into chronic and short term evaluation of hybrid graft materials.

Three and four mm. hybrid grafts were sutured (implanted) into the carotid and femoral arteries of dogs for periods ranging from 1 second to 2 months. (1 sec., 2 hr., 1 week, 1 month, 2 months).

Six mm. hybrid grafts were implanted into the abdominal aorta of dogs for time periods ranging from 1 month to 1 year (1 month, 6 months, 9 months, 1 year).

The hybrid grafts were removed from their sterile solutions and placed into a sterilized 500 ml. beaker and sequentially washed with 250 ml. of sterile saline 20×. The grafts were then placed into a sterile stainless steel bin containing 1.5 liters of sterile saline, until placed in a sterile field and implanted.

Prior to implantation, the end pieces were cut to provide an even surface for anastomosis and samples for controls, culturing and SEM studies to determine efficiency of coating and function.

End-to-end anastomosis was carried out using a running Carrell suture with 4–0 cardiovascular Dacron or other material. Precise anastomosis was carried out in all cases.

Percent patency has been determined using a semiquantitative scale. This has been determined by taking the cross sectional view of a graft and dividing it into equal concentric circles of ¼ D from the wall of the vessel. Thus, it is now possible to quantify the amount of thrombus formed by measuring the depth of the thrombus then relating it to the total cross sectional area. The numbers generated by this technique are expressed in terms of percentage of the entire vessel.

Post Implantation Studies

The graft-hybrid materials were analyzed using (1) scanning electron microscopy (SEM), (2) light microscopy and (3) histological staining. Patency was determined using the aforementioned semi-quantitative technique.

Scanning Electron Microscopy (SEM)

SEM's were performed on the grafts before implantation and after removal using a Phillip's scanning electron microscope at 200×, 10K× and 20K× magnifications. With these magnifications, it is possible to resolve and differentiate platelets, erythrocytes, and leukocytes, and white blood cells and to visualize protein (including fibrin) deposition.

The SEM's were used to detect (1) efficiency of hybridization (to determine structural flaws in the coatings) and (2) to determine visible evidence of the type of blood prostheses interfacial reactions.

Histological and Light Microscopic Evaluations

Graft sections were evaluated by the use of several standard histological stains including Hemotoxylan and Eosin (H&E) Van Geisen (Elastic VG stain), PTAH and Trichrome. Each stain specifically detects the type of material adhering to the graft or removal from the animal by the colors which are produced when the staining solution is in contact with the biological material. H&E is used to visualize cellular entities and to demonstrate if an inflamatory response has occurred and if polynucleated cells or lymphocytes are present.

EVG stain is used to illustrate fibroblastic invasion and to dye the collagen present. For instance, Trichrome stains collagen blue. PTAH stain is used to demonstrate the presence of fibrin.

Results

The following table illustrates the patency levels of the various hybrid grafts.

| Type | % Patency of Hybrid Grafts | | | | Dacron Support |
|---|---|---|---|---|---|
| | 1 Sec | 2 Hr | 1 Mon | 9 Mon | |
| Agar | 90 | 70 | — | — | Microknit® |
| Acrylamide | 95 | 80 | — | — | " |
| A Unmod | 99 | 99 | 95 | — | " |
| (−) | 99 | 99 | 99 | X | " |
| G Unmod | 99 | 80 | 80 | — | " |
| (−) | 99 | 99 | 99 | X | " |
| A&G Unmod | 95 | 90 | 90 | — | " |
| (−) | 99 | 99 | 99 | X | " |
| Al | 99 | 99 | 99 | X | WVE Old Weslowski Weave Knit |
| Al | 99 | 99 | 99 | X | |

A — Albumin
G — Gelatin

Table 1: Relates the type of hybridization, time of implantation and percent patency. Column 1 is the type of "coating" and subsequent negative charging. The next 4 columns are the time parameters at which they were analyzed. The numbers represent the % of patency. A check indicates that the graft is still functioning in-vivo. A—indicates that that parameter was not measured. The last column is the type of Dacron support used with that particular modification.

The following figures are SEM studies of the following hybrid grafts before and after implantation, negative charged and unmodified, of (i) Albumin (A) coated grafts, (ii) Gelatin (G) coated grafts, (iii) a 50/50 mixture of albumin and gelatin in a concentration of 3% each (AG), (iv) acrylamide coated graft (ACD), (v) agar-agar coated grafts (AGR), and CVD aluminum coated grafts (Al).

FIG. 1(A) shows scanning electron micrographs of a polymerized protein, namely, of an albumin Dacron hybrid graft. This series of photographs demonstrates the homogenicity of a protein on Dacron surface.

FIG. 1(B) shows scanning electron micrographs of a protein-gelatin Dacron hybrid graft. The photographs show a homogeneous surface prior to and after exposure of the surface to blood for 1 second.

FIG. 2(A) shows scanning electron micrographs of a gelatin-Dacron hybrid graft. These photographs reveal minor cracking of the polymerized surface at high (10K×) magnification.

FIG. 2(B) shows scanning electron micrographs of a gelatin-Dacron hybrid graft. Following polymerization of the hybrid, the surface was chemically treated (succinylating) to produce a net negative surface charge. These micrographs indicate that the negative surface at 1 second, 2 hours, and 1 month is far less reactive then the unmodified hybrid surface. The unmodified surface has a dense amount of cellular protein deposition thereon, while the negatively charged surface attracts fewer cellular aggregates. The patency rate for the negatively charged grafts was approximately 90% as opposed to 60% for the unmodified surface at 2 hours.

FIG. 3(A) shows the smooth structure of an agar coated Microknit ® Dacron graft and FIG. 3(B) shows implantation results of a protein-gelatin Dacron hybrid graft. The SEM photographs reveal that the protein-gelatin negatively charged hybrid is less reactive at 1 second, 2 hours and 1 month than the unmodified graft. Many erythrocytes entrapped in a protein matrix can be seen in the unmodified surface while the negatively charged surface possesses few red cells and no visible platelets. Patency rates for the negatively charged grafts was approximately 90% as opposed to 70% for the unmodified grafts at 2 hours.

FIG. 4 shows scanning electron micrographs of an aluminum coated Dacron hybrid graft. Following implantation, the graft was examined. Little protein deposition could be seen. A layer of cells which appear to be erythrocytes and monocytes bound to fibrinogin seem to be sparsely coating the surface. The metallic coating may be toxic to cellular elements, as the monocytes are atypical. The patency rate in all cases was 100%.

FIG. 5 shows scanning electron micrographs of an agar coated-Dacron hybrid. Implantation results indicate a reactive surface with cellular and protein deposition. Patency rates were 80% at 1 sec. and 40% at 2 hours.

FIG. 6(A) shows an aluminum coated Dacron prosthesis exposed to blood for 1 second. The fibrils are virtually free of cellular elements with the exception of a very few erythrocytes and leukocytes with a few visible platelets attached as well. At 10K×magnification, the single large cell appears to be a toxic neutrophile. The remainder of the photograph displays proteiniated aluminum substrate. At 2 hours, the cells are smaller and appear to be crenating.

FIG. 6(B) shows further magnifications at 1K× and these reveal a few crenating cells with a very thin layer of protein attached to the aluminized Dacron fabric. These cells are completely gone by 1 month, the fabric being joined by what appears to be a thin amorphous layer of protein. This may be proteinated aluminum.

Histological evaluation was carried out in parallel to the SEM studies. In all cases, these was no evidence of (1) polynucleated cells or lymphocytes or, (ii) inflamatory response. All grafts had fibroblastic invasion. Type A presents the most explicit example. In all cases, protein coating was firmly attached to the Dacron. Coating of each strand of Dacron was also established.

The different histological responses to the various types of hybrid grafts are described in Table II.

TABLE II

| A Summary of Histological Study of Hybrid Grafts | | |
|---|---|---|
| Graft Type | Patency | Description ++ |
| Al | 99% | Revealed no evidence of cells or fibrin |
| A | 99% (1 month) | Coating uniform with no evidence of separation. Unmodified: had few cellular elements which were loosely attached to a proteineous material which is not fibrin. This may be a coincidental attachment of cells. Modified: revealed no evidence of cells. The globular objects which appear on the SEM are not cells. There is no trace of fibrin. |
| G | 80% (unmodified) 2 Hr. & 1 Mon. 99% | There is fibrin which is attached to the wall at a depth of .5 to 1 mm. |

TABLE II-continued

A Summary of Histological Study of Hybrid Grafts

| Graft Type | Patency | Description ++ |
|---|---|---|
| | (neg. charge) [1 sec.] 1 mon. | Has few cellular elements which are widely dispersed and well passivated in a thin protein layer which is not fibrin. |
| A & G | 90% | Unmodified: These are cellular elements which is followed by a fibrin layer. In 2 hours, there is evidence of a building new cellular and fibrin layer. |
| | 99% (1 month) | Modified: There is evidence of a few cellular elements which are passivated by a thin non-fibrin protein layer. |
| Agar | 75–80% | In 1 sec., there is evidence of an instantaneous thrombus which is primarily a chain of fibrin. There are a few cells present at this time. At 2 hours - there is a large deposit of cellular elements plus fibrin formation on the graft. |
| Acrylamide | 75% | In 1 sec. and 2 hours this graft produced a peculiar thrombus. The thrombus had many more cellular elements and markedly less fibrin than did any of the other thrombi producing surfaces. |

There will now be obvious to those skilled in the art many modifications and variations of the methods and materials set forth hereinabove. These modifications and variations will not depart from the scope of the invention if defined by the following claims.

What is claimed is:

1. A prosthesis suitable for implantation in a bloody environment, said prosthesis comprising a surface material adapted for exhibiting a regular and periodic surface charge characteristic in said environment, and prosthesis means supporting said surface material and adapted to perform a prosthetic function in said environment, said surface material being agar, said prosthesis means being of Dacron.

2. A prosthesis as claimed in claim 1 wherein said Dacron is of a woven structure.

* * * * *